United States Patent [19]

Pews et al.

[11] Patent Number: 4,894,085

[45] Date of Patent: Jan. 16, 1990

[54] HERBICIDAL CYANOFLUOROPHENOXYPHENOXYALKANOIC ACIDS AND DERIVATIVES THEREOF

[75] Inventors: R. Garth Pews, Midland, Mich.; Lucinda A. Jackson, Pleasant Hill, Calif.; Chrislyn M. Carson, Midland, Mich.

[73] Assignee: The Dow Chemical Company, Midland, Mich.

[21] Appl. No.: 277,619

[22] Filed: Nov. 29, 1988

Related U.S. Application Data

[63] Continuation-in-part of Ser. No. 82,030, Aug. 5, 1987, abandoned.

[51] Int. Cl.$^4$ ............................................. A01N 37/40
[52] U.S. Cl. ....................................... 71/105; 558/414
[58] Field of Search ........................... 558/414; 71/105

[56] References Cited

U.S. PATENT DOCUMENTS

| | | | |
|---|---|---|---|
| 4,134,753 | 1/1979 | Horlein et al. | 71/106 |
| 4,309,210 | 1/1982 | Quadranti et al. | 71/93 |
| 4,349,377 | 9/1982 | Durr et al. | 71/98 |
| 4,394,327 | 7/1983 | Rohr et al. | 260/455 |
| 4,441,913 | 4/1984 | Aya et al. | 71/94 |
| 4,536,321 | 8/1985 | Sugimori et al. | 252/299.63 |
| 4,550,192 | 10/1985 | Rogers et al. | 560/62 |
| 4,600,432 | 7/1986 | Akahira et al. | 71/94 |

FOREIGN PATENT DOCUMENTS

| | | |
|---|---|---|
| 2646124 | 10/1976 | Fed. Rep. of Germany . |
| 2730591 | 12/1978 | Fed. Rep. of Germany . |
| 2834744 | 3/1979 | Fed. Rep. of Germany . |
| 1142534 | 12/1976 | Japan . |
| 005935 | 1/1979 | Japan . |
| 031758 | 2/1984 | Japan . |
| 9116255 | 7/1984 | Japan . |
| 62-53 | 1/1987 | Japan . |
| 62-12755 | 1/1987 | Japan . |
| 7013949 | 3/1987 | Japan . |
| 1545001 | 4/1979 | United Kingdom . |
| 8604895 | 8/1986 | World Int. Prop. O. . |

*Primary Examiner*—William R. Dixon, Jr.
*Assistant Examiner*—Jerry D. Johnson
*Attorney, Agent, or Firm*—Craig E. Mixan; Ronald G. Brookens; Richard G. Waterman

[57] ABSTRACT

Novel 2-(4-(2'-fluoro-4'-cyanophenoxy)phenoxy)alkanoic acids and agriculturally acceptable derivatives thereof are selective postemergent herbicides for the control of grassy weeds in valuable crops. The novel herbicides are surprisingly selective, i.e., exhibit little or no phytotoxic effects, to wheat, barley and especially rice at concentrations that control undesired weed grasses.

35 Claims, No Drawings

HERBICIDAL CYANOFLUOROPHENOXYPHENOXYALKANOIC ACIDS AND DERIVATIVES THEREOF

CROSS-REFERENCE TO RELATED APPLICATION

This application is a continuation-in-part of applicants' copending application Ser. No. 082,030, filed Aug. 5, 1987 now abandoned.

BACKGROUND OF THE INVENTION

The present invention relates to novel cyanofluorophenoxyphenoxyalkanoates and derivatives thereof which are useful as herbicides. The present invention also relates to herbicidal compositions containing these novel compounds and to the methods of using these compounds for the postemergent control of grassy weeds in non-crop areas, in broadleaf crops, as well as in the presence of certain valuable grass crops such as wheat, barley and especially rice. The invention is also directed to the novel stereoisomers of such compounds, the R-enantiomer having exceptional activity.

Various 2-(4-(cyano- and carbamylphenoxy)phenoxy)alkanoic acids and derivatives thereof are known as herbicidal agents. For example, Japanese Kokai Tokkyo Koho 79 05,935 discloses various 2-(4-(cyano- and carbamylphenoxy)phenoxy)alkanoic acids and derivatives thereof in which the cyano- and carbamylphenoxy group is further substituted with chlorine, bromine or iodine. British patent 1,545,001 discloses 2-(4-(cyanophenoxy)phenoxy)alkanoic acids and certain derivatives thereof in which the cyanophenoxy group may be further substituted with halogen, trifluoromethyl or cyano. The particularly preferred substituents are taught to be chlorine and trifluoromethyl. U.S. Pat. No. 4,550,192 discloses certain herbicidal 2-(4-(2'-fluoro-4'-halo-, haloalkyl- and haloalkoxyphenoxy)phenoxy)alkanoic acids and derivatives thereof but does not disclose cyano substitution.

Heretofore, 2-(4-(2'-fluoro-4'-cyanophenoy)phenoxy)alkanoic acids and agriculturally acceptable derivatives thereof have not been disclosed.

SUMMARY OF THE INVENTION

The present invention is directed to cyanofluorophenoxyphenoxyalkanoates of the Formula (I):

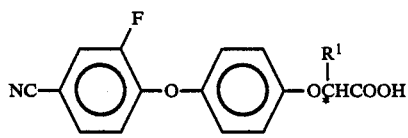

wherein $R^1$ represents a $C_1$–$C_3$ alkyl group and agriculturally acceptable derivatives, particularly the salts and esters of the alkanoic acid group thereof. The "*" denotes a chiral carbon atom. Compounds with such chiral atoms can exist as enatiomers, i.e., mirror-image isomers that are not superimposable.

The compounds of the above Formula (I), hereinafter referred to as "active ingredients", have been found to be active as herbicides in the presence of broadleaf crops and are unexpectedly superior in activity compared to compounds known in the art. Furthermore, the compounds of Formula (I) are surprisingly selective to certain cereal crops, especially rice, i.e., substantially non-phytotoxic to rice. Accordingly, the present invention also encompasses herbicidal compositions containing one or more of the active ingredients as well as methods of controlling unwanted vegetation. Such methods comprise, for example, applying a herbicidally effective amount of one or more active ingredients postemergently to the locus of the undesired vegetation, and particularly to the locus where a valuable crop is to germinate and grow.

DETAILED DESCRIPTION OF THE INVENTION

The term "herbicide" is used herein to mean an active ingredient which controls or adversely modifies the growth of plants. By "growth controlling" or "herbicidally-effective" amount is meant an amount of active ingredient which causes an adversely modifying effect and includes deviations from natural development, killing, regulation, desiccation, retardation and the like.

The term "plants", when used herein, is meant to include emerging seedlings, rhizomes, stolons and other underground propagules, as well as established vegetation.

The term "agriculturally acceptable derivatives", when used to describe the active ingredients disclosed herein, is meant to encompass any salt, amide, ester or other derivative of said active ingredients (acids) which (1) does not substantially affect the herbicidal activity of said active ingredients, and (2) is or can be hydrolyzed and/or oxidized in plants or soil to the alkanoic acid moiety of Formula (I) that, depending on the pH, is in the dissociated and/or undissociated form.

Agriculturally acceptable derivatives of the active ingredients, as defined hereinabove, include but are not limited to compounds of Formula (II):

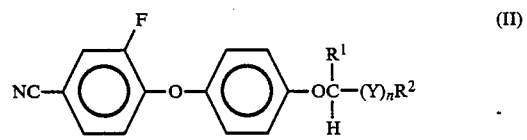

wherein

Y represents a saturated or unsaturated alkyl group containing an even number of carbon atoms, preferably from 2 to 6 carbon atoms;

n represents 0 or 1;

$R^1$ represents a $C_1$–$C_3$ alkyl group; and $R^2$ represents moieties corresponding to one of the following formulae:

-continued

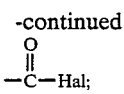 (4)

wherein Hal is halogen;

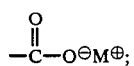 (5)

wherein M represents a metallic cation, ammonium cation or an organic amine cation, typically, but not exclusively, containing alkyl (saturated or unsaturated), alicyclic, heterocyclic or aromatic groups, all unsubstituted or substituted with various other groups not limited to, but including, halo, cyano, nitro and unsubstituted or substituted thiol, hydroxy, amino or carboxyl groups and, additionally, alicyclic, heterocyclic and aromatic groups substituted with unsubstituted or substituted saturated or unsaturated alkyl groups, for example, trifluoromethyl, chloromethyl, cyanomethyl and vinyl;

—CH$_2$OR$^3$; (6)

 (7)

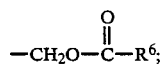 (8)

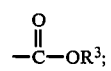 (9)

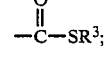 (10)

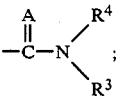 (11)

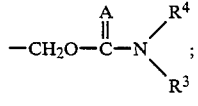 (12)

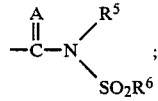 (13)

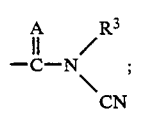 (14)

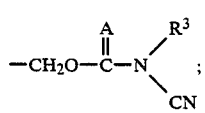 (15)

 (16)

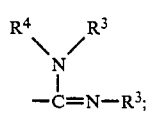 (17)

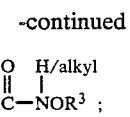 (18)

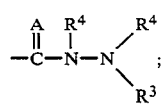 (19)

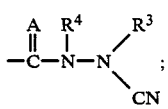 (20)

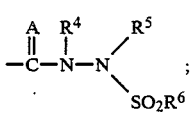 (21)

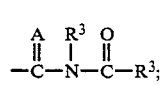 (22)

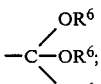 (23)

—C(SR$^6$)$_3$; (24)

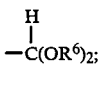 (25)

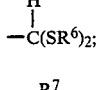 (26)

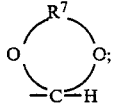 (27)

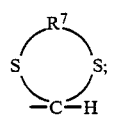 (28)

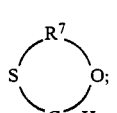 (29)

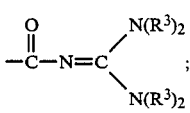 (30)

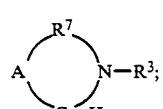 (31)

wherein
W represents —OR$^6$, —SR$^6$ or halogen;
A represents O or S;
R$^3$ represents H or R$^6$;
R$^4$ represents H, alkoxy or R$^6$;
R$^5$ represents H, a metallic cation or R$^6$; and $R^6$ represents an alkyl (saturated or unsaturated), alicyclic, heterocyclic or aromatic group, unsubstituted or substituted with various other groups not limited to, but including, halo, cyano, nitro, unsubstituted or substituted alkoxy, unsubstituted or substituted thiol, hydroxy, amino or carboxyl groups and, additionally, alicyclic, heterocyclic and aromatic groups substituted with unsubstituted or substituted saturated or unsaturated alkyl groups, for example, trifluoromethyl, chloromethyl, cyanomethyl and vinyl;

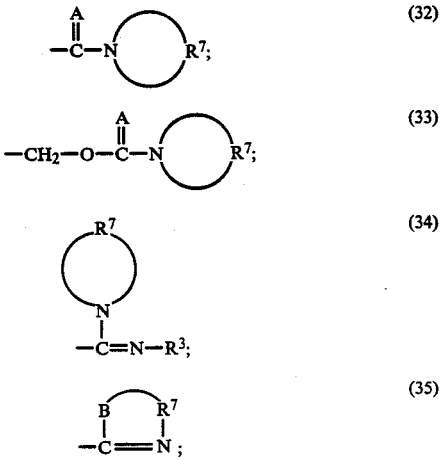

(32)

(33)

(34)

(35)

wherein
B is O, S or N; or (36)

where $R^7$ completes an unsubstituted or substituted heterocyclic ring system and A represents O or S.

In Formula (II) above, the aliphatic groups preferably contain 1 to 6 carbon atoms, the alkenyl and alkynyl groups preferably contain 2 to 6 carbon atoms, the alicyclic groups preferably contain 3 to 6 carbon atoms and the aromatic moiety is preferably phenyl, although other ring systems, including heterocyclic ring systems, may be employed if desired.

$R^2$ is preferably a carboxylic acid group, an alkali or alkaline earth metal salt thereof, an ammonium or organic amine salt thereof, an amide or lower alkyl amide thereof or a lower alkyl ester thereof, wherein "lower alkyl" includes straight, branched or cyclic saturated or unsaturated alkyl groups containing no more than 6 carbon atoms. Preferably, n is 0 and $R^1$ is methyl.

The preferred compounds are of Formula (III)

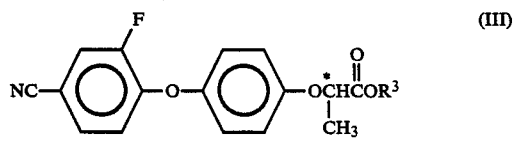

(III)

wherein $R^3$ is hydrogen, a metallic cation, methyl, ethyl, propyl, iso-propyl, n-butyl, iso-butyl or sec-butyl. The most preferred compounds are the R-enantiomers thereof.

The fluorophenoxyphenoxy compounds of Formula (II) above, also referred to as "active ingredients", can be prepared employing procedures analogous to well-known procedures for preparing known phenoxyphenoxyalkanoic acids and derivatives thereof. U.S. Pat. Nos. 4,550,192, 4,600,432 and British Pat. No. 1,545,001 describe such procedures and are all incorporated herein by reference. For example, some of the compounds of Formula (II) can be prepared by reacting 3,4-difluorobenzonitrile with an alkali or alkaline earth metal salt of an appropriate (4-hydroxyphenoxy)alkanoic acid derivative in a suitable solvent medium, such as dimethylsulfoxide (DMSO), dimethylformamide (DMF), N-methylpyrrolidone, hexamethylphosphoramide (HMPA) or tetrahydrofuran (THF). The reaction is advantageously carried out at a temperature from about 20° C. to about 150° C. This reaction can be characterized as follows:

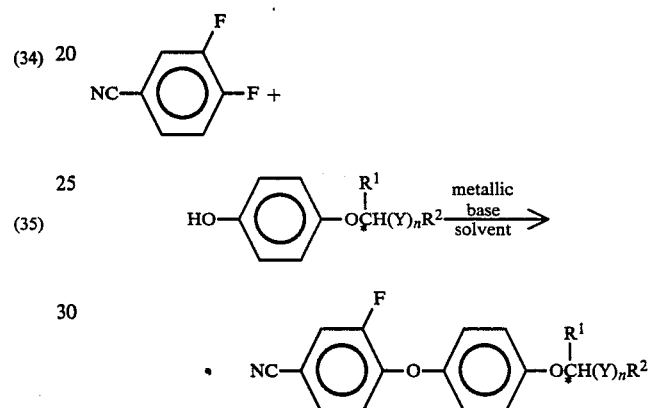

wherein $R^1$, Y, n and $R^2$ are as hereinbefore defined. This reaction is preferred for preparing compounds of Formula (III). The metallic base is a base, such as, for example, NaOH, KOH, $Na_2CO_3$ or $K_2CO_3$.

Alternatively, some of the compounds of Formula (II) can be prepared by reacting an alkali or alkaline earth metal salt of 4-(2'-fluoro-4'-cyanophenoxy)phenol with an appropriate alkanoate derivative containing a leaving group (Br, Cl or alkyl or aryl sulfonate) in a suitable solvent medium, such as, DMSO, DMF, THF, HMPA or N-methylpyrrolidone. This reaction is advantageously carried out at a temperature of from about 20° C. to about 150° C. This reaction can be characterized as follows:

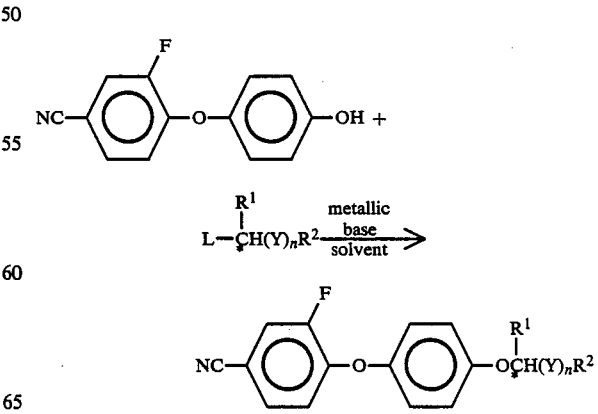

wherein $R^1$, Y, n and $R^2$ are as hereinbefore defined and L is Br, Cl or $R^8SO_2O$ where $R^8$ is $C_1-C_4$ alkyl or unsubstituted or substituted phenyl. The metallic base is a base, such as, for example, NaOH, KOH, Na₂CO₃ or K₂CO₃.

The corresponding R-enantiomers may be prepared by using optically active starting materials. For example, the desired R-enantiomer may be prepared either by reacting 3,4-difluorobenzonitrile with the R-enantiomer of the (4-hydroxyphenoxy)alkanoic acid derivative or by reacting the 4-(2'-fluoro-4'-cyanophenoxy)-phenol with the S-enantiomer of the appropriate alkanoate derivative, e.g., a 2-halopropionate derivative. Alternatively, the R-enantiomers may be obtained from the racemate by conventional resolution procedures.

4-(2'-Fluoro-4'-cyanophenoxy)phenol and the alkali metal salts thereof are novel intermediate compounds and are within the scope of the present invention. These intermediates can be prepared by reacting 3,4-difluorobenzonitrile with hydroquinone in a suitable solvent medium such as, DMSO, DMF, THF, HMPA or N-methylpyrrolidone in the presence of a metallic base. The reaction is advantageously carried out at a temperature from about 20° C. to about 150° C. and the metallic base is a base, such as, for example, NaOH, KOH, Na₂CO₃ or K₂CO₃. The reaction can be characterized as follows:

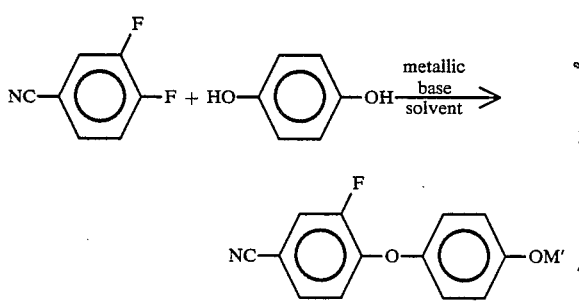

where M' is hydrogen, Na⊕ or K⊕. Alternatively, these intermediates can be prepared by reacting 3,4-difluorobenzonitrile with a stoichiometric amount of 4-methoxyphenol under similar conditions. The methyl ether of the resulting 4-(2'-fluoro-4'-cyanophenoxy)methoxybenzene can be subsequently cleaved with hydrobromic or hydroiodic acid in a suitable solvent medium, such as, for example, acetic acid/acetic anhydride. The reaction is advantageously carried out at a temperature from about 0° C. to about 120° C. The reaction can be characterized as follows:

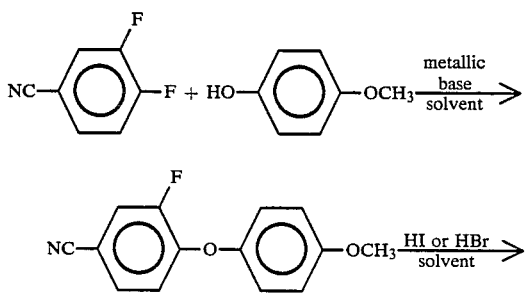

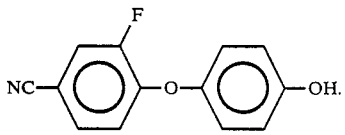

Not all of the above derivatives of Formula (II) can be prepared directly by the processes described hereinabove because they may be susceptible to transformations under the reaction conditions employed. Nevertheless, they can be made by conventional processes generally known to those skilled in the art and as described in U.S. Pat. Nos. 4,565,568 and 4,550,192 and in the references contained therein. For example, the corresponding acid chlorides can be reacted with alcohols or amines to make the desired esters or amides; with a Grignard reagent to make the desired ketone; with KSH to make the desired thiol acid.

Once prepared, the compounds of the present invention are recovered employing standard well-known extraction and purification techniques, such as, for example, solvent extraction, crystallization or chromatographic separation.

The following examples illustrate the practice of the present invention but should not be construed as limiting its scope.

EXAMPLE 1

Preparation of methyl 2-(4-(2'-fluoro-4'-cyanophenoxy)phenoxy)propionate

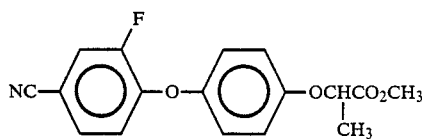

(A) Methyl 2-(4-hydroxyphenoxy)propionate (5.88 grams (g); 0.03 moles) was dissolved in 50 milliliters (mL) of dimethyl sulfoxide (DMSO) and 2.40 g of 50 percent NaOH (0.03 moles) was added. The mixture was warmed to 80° C. and 4.17 g (0.03 moles) of 3,4-difluorobenzonitrile (Aldrich Chemical Company) was added. The solution was heated and stirred at 80° C. for 4 hours (hr). After cooling, the product was isolated by extraction with ethyl acetate. Unreacted phenolic starting material was removed by washing with dilute NaOH. Unreacted 3,4-difluorobenzonitrile was removed from the concentrated extract utilizing a Kugelrohr. The viscous oil that remained eventually crystallized on standing, m.p. 57°–58° C.

| | | |
|---|---|---|
| mass spectrum: | m/e 315 | |
| infrared: | 2280 cm⁻¹ | (CN) |
| | 1780 cm⁻¹ | 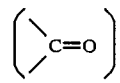 |
| nuclear magnetic resonance: | | δ 1.65 (d, 3, CH₃) |
| | | δ 3.75 (s, 3, OCH₃) |
| | | δ 4.75 (q, 1, CH) |
| | | δ 6.7–7.6 (m, 7, aromatic) |

(B) Hydroquinone (5.5 g; 0.05 moles) was dissolved in 50 mL of dimethyl sulfoxide and 8.0 g (0.1 moles) of 50 percent NaOH was added to the solution. The solution was heated and stirred at 80° C. and 7.0 g (0.05 moles) of 3,4-difluorobenzonitrile in 10 ml of dimethyl sulfoxide was added dropwise. The reaction mixture was maintained at 80° C. for 2 hr. After cooling, the reaction mixture was poured into cold dilute HCl. The precipitate that formed was filtered and dried. The desired 4-(2'-fluoro-4'-cyanophenoxy)phenol was purified by elution with chloroform from a silica gel column. The isolated product was obtained as a white solid, m.p. 144°–146° C.

| | |
|---|---|
| mass spectrum | m/e 229 |
| infrared | 3400 cm$^{-1}$ (OH) |
| | 2240 cm$^{-1}$ (CN) |
| nuclear magnetic resonance | δ(6–7, m, aromatic) |

The 4-(2'-fluoro-4'-cyanophenoxy)phenol (2.29 g/0.01 moles) was dissolved in 25 mL of dimethyl sulfoxide and 2.0 g of $K_2CO_3$ was added to the solution. The mixture was stirred and 2.46 g (0.011 moles) of the benzenesulfonate of methyl lactate [$CH_3CH(OSO_2C_6H_5)CO_2CH_3$] was added. The reaction mixture was heated at 80° C. with stirring for 4 hr. After cooling, the product was isolated by extraction with benzene. The infrared and nuclear magnetic resonance spectra confirmed that the product was identical to that prepared in Example 1-A.

EXAMPLE 2

Preparation of the R-enantiomer of methyl 2-(4-(2'-fluoro-4'-cyanophenoxy)phenoxy)propionate The R-enantiomer was prepared by substantially the same procedure as described in Example 1-A except that anhydrous $K_2CO_3$ was used as the base and optically active R-methyl 2-(4-hydroxyphenoxy)propionate was used as the starting material. The product was a solid with a m.p. of 50°–53° C. An enantiomer ratio of 88.7 R/11.3 S was determined by HPLC using a commercially available Chiracel OK column (cellulose tricinnamate; available from Daicel).

EXAMPLE 3

Preparation of 2-(4-(2'-fluoro-4'-cyanophenoxy)phenoxy)propionic acid

A solution of 1.5 g (4.8 mmoles) of methyl 2-(4-(2'-fluoro-4'-cyanophenoxy)phenoxy)propionate and 0.4 g (6.1 mmoles) of 85 percent KOH in 30 mL of methanol was stirred at room temperature for 24 hr. The methanol was evaporated under reduced pressure and the residue was dissolved in water. The solution was acidified with 37 percent HCl to pH 2 and extracted with 100 ml of ether. The ether extract was dried over anhydrous $MgSO_4$, filtered and concentrated under reduced pressure to a white solid. The solid was recrystallized from a 4:1 mixture of hot methylcyclohexane and toluene to give 1.1 g of a fine white powder, m.p. 145°–146° C.

| Analysis | | | |
|---|---|---|---|
| | C | H | N |
| Calculated for $C_{16}H_{12}FNO_4$ | 63.78 | 4.01 | 4.65 |
| Found | 63.71 | 4.09 | 4.55 |

EXAMPLE 4

Preparation of the R-enantiomer of 2-(4-(2'-fluoro-4'-cyanophenoxy)phenoxy)propionic acid The R-enantiomer was prepared by substantially the same procedure as described in Example 3 except that the R-enantiomer of methyl 2-(4-(2'-fluoro-4'-cyanophenoxy)phenoxy)propionic acid was used as the starting material. The product was a solid with a melting range of 115°–136° C. An enantiomer ratio of 88.5 R/11.5 S was determined by HPLC.

EXAMPLE 5

Preparation of the sodium salt of the R-enantiomer of 2-(4-(2'-fluoro-4'-cyanophenoxy)phenoxy)propionic acid 2-(4-(2'-Fluoro-4'-cyanophenoxy)phenoxy)propionic acid (1.60 g; 0.005 mol) [R/S: 97/3] was dissolved in 50 mL of methanol and 50 percent NaOH (0.40 g; 0.005 mol) in 50 mL of methanol was added. The methanol was removed under reduced pressure to give a white solid, m.p. 209°–212° C.

| | | |
|---|---|---|
| infrared (Nujol): | 1525 cm$^{-1}$ | ($\diagdown$C=O$\diagup$) |
| | 2255 cm$^{-1}$ | (CN) |
| nuclear magnetic resonance (DMSO-d$_6$): | | δ 1.35 (d, 3, CH$_3$) |
| | | δ 4.30 (q, 1, CH) |
| | | δ 6.75–8.20 (m, 7, aromatic) |

EXAMPLE 6

Preparation of the ammonium salt of the R-enantiomer of 2-(4-(2'-fluoro-4'-cyanophenoxy)phenoxy)propionic acid 2-(4-(2'-Fluoro-4'-cyanophenoxy)phenoxy)propionic acid (1.60 g; 0.005 mol) [R/S: 97/3] was dissolved in methanol and saturated with anhydrous ammonia at room temperature. After evaporation of the solvent, the remaining solid was slurried in carbon tetrachloride-dichloromethane and filtered, m.p. 155°–170° C. (decomp).

| | | |
|---|---|---|
| infrared (Nujol): | 1600 cm$^{-1}$ | ($\diagdown$C=O$\diagup$) |
| | 2555 cm$^{-1}$ | (CN) |
| nuclear magnetic resonance (DMSO-d$_6$): | | δ 1.35 (d, 3, CH$_3$) |
| | | δ 4.30 (q, 1, CH) |
| | | δ 6.70–8.20 (m, 11, aromatic & NH$_4$) |

EXAMPLE 7

Preparation of the triethylammonium salt of the R-enantiomer of 2-(4-(2'-fluoro-4'-cyanophenoxy)phenoxy)propionic acid 2-(4-(2'-Fluoro-4'-cyanophenoxy)phenoxy)propionic acid (1.60 g; 0.005 mol) [R/S: 97/3] was dissolved in methanol and excess triethylamine was added to the solution. After evaporation of the solvent, the product was isolated as a viscous oil.

| nuclear magnetic resonance: | δ 1.18 (t, 9, CH$_2$CH$_3$) |
|---|---|
| | δ 1.40 (d, 3, CH$_3$) |
| | δ 3.00 (q, 6, CH$_2$CH$_3$) |
| | δ 4.60 (q, 1, CH) |
| | δ 6.65–7.95 (m, 7, aromatic) |

EXAMPLE 8

Preparation of 2-(4-(2'-fluoro-4'-cyanophenoxy)phenoxy)propionic acid

Powdered anhydrous K$_2$CO$_3$ (48 g) was added to 150 mL of dimethyl sulfoxide and 2-(4-hydroxyphenoxy)-propionic acid was added to the dimethyl sulfoxide slurry. The mixture was heated to 60° C. and stirred for 1 hr. 3,4-Difluorobenzonitrile (20 g) was added to the mixture, the temperature was increased to 85° C., and the mixture was stirred for an additional 4 hr. After cooling, the salt was filtered and 20 mL of water added to the filtrate. The pH of the aqueous solution was adjusted to ~1.0 with dilute hydrochloric acid. The aqueous solution was extracted with toluene (2X) and the combined organic extract washed with 100 mL of 1.0N HCl. The solvent was dried with MgSO$_4$ and the solvent evaporated to give crude acid. The crude acid was recrystallized from toluene to give product m.p. 145°–146° C.

EXAMPLE 9

Preparation of 2-(4-(2'-fluoro-4'-cyanophenoxy)phenoxy)propionic acid chloride 2-(4-(2'-Fluoro-4'-cyanophenoxy)phenoxy)propionic acid (29.3 g; 0.097 mol) was dissolved in 200 mL of toluene and 1 mL of dimethyl formamide was added as a catalyst. Thionyl chloride (approx. 15 g) was added to the stirred solution at room temperature and the solution was stirred for 2 hr. The temperature was increased to 80°–85° C. for approximately 1.5 hr. After cooling and evaporation of volatiles on a rotary evaporator, a viscous liquid was obtained which solidified on standing, m.p. 55°–58° C.

| infrared (Nujol): | 1775 cm$^{-1}$ | 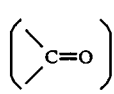 |
|---|---|---|
| | 2200 cm$^{-1}$ | (CN) |
| nuclear magnetic resonance (CDCl$_3$): | δ 1.80 (d, 3, CH$_3$) | |
| | δ 5.00 (q, 1, CH) | |
| | δ 6.80–7.70 (m, 7, aromatic) | |

EXAMPLE 10

Preparation of n-butyl 2-(4-(2'-fluoro-4'-cyanophenoxy)phenoxy)propionate 2-(4-(2'-Fluoro-4'-cyanophenoxy)phenoxy)propionic acid chloride (3.19 g; 0.01 mol) was dissolved in 25 mL of carbon tetrachloride. n-Butanol (0.74 g; 0.01 mol) and 1 mL of pyridine were dissolved in an equivalent amount of solvent. The acid chloride solution was added dropwise to the alcohol-pyridine solution at room temperature over a 15 minute period. After stirring at room temperature for 1 hr, the product was isolated by extraction as a viscous oil. Gas-chromatographic analysis indicated a purity in excess of 99 percent.

mass spectrum: m/e 357

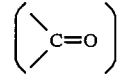

| infrared (Nujol): | 1750 cm$^{-1}$ | (C=O) |
|---|---|---|
| | 2250 cm$^{-1}$ | (CN) |
| nuclear magnetic resonance (CDCl$_3$): | δ 0.90 (t, 3, CH$_2$CH$_3$) | |
| | δ 1.10–1.50 (m, 4, CH$_2$CH$_2$CH$_3$) | |
| | δ 1.60 (d, 3, CH$_3$) | |
| | δ 4.20 (t, 2, OCH$_2$) | |
| | δ 4.70 (q, 1, CH) | |
| | δ 6.70–7.60 (m, 7, aromatic) | |

EXAMPLE 11

Preparation of (1-methylethyl) 2-(4-(2'-fluoro-4'-cyanophenoxy)phenoxy)propionate The procedure for Example 10 was repeated substituting an equivalent amount of iso-propyl alcohol for the n-butanol. The product was isolated as a viscous oil whose purity exceeded 99% by gas chromatographic analysis.

| Calculated For: | C$_{19}$H$_{18}$FNO$_4$ | 343 |
|---|---|---|
| Found | GC—MS | 343 |
| nuclear magnetic resonance (CDCl$_3$): | δ (1.25 (dd, 6, HC(CH$_3$)$_2$) | |
| | δ 1.58 (d, 3, HCCH$_3$) | |
| | δ 4.75 (a, 1, CH) | |
| | δ 5.10 (m, 1, CH(CH$_3$)$_2$) | |
| | δ 6.75–7.65 (m, 7, aromatic) | |

EXAMPLE 12

Preparation of (1-methylpropyl) 2-(4-(2'-fluoro-4'-cyanophenoxy)phenoxy)propionate The procedure for Example 10 was repeated substituting an equivalent amount of sec-butyl alcohol for the n-butanol. The product was isolated as a viscous oil whose purity exceeded 99% by gas chromatographic analysis.

| Calculated For: | C$_{20}$H$_{20}$FNO$_4$ | 357 |
|---|---|---|
| Found: | GC—MS | 357 |
| nuclear magnetic resonance (CDCl$_3$): | δ 0.95 (t, 3, CH$_2$C$\underline{H}_3$) | |
| | δ 0.7–1.40 (m, 2, C$\underline{H}_2$) | |
| | δ 1.20 (d, 3, CHC$\underline{H}_3$) | |
| | δ 1.75 (d, 3, CHC$\underline{H}_3$) | |
| | δ 4.75 (m, 2, C$\underline{H}$CH$_3$) | |
| | δ 6.75–7.75 (m, 7, aromatic) | |

EXAMPLE 13

Preparation of (2-methylpropyl) 2-(4-(2'-fluoro-4'-cyanophenoxy)phenoxy)propionate The procedure for Example 10 was repeated substituting an equivalent amount of iso-butyl alcohol for the n-butanol. The product was isolated as a viscous oil whose purity by gas chromatographic analysis exceeded 99%.

| Calculated For: | C$_{19}$H$_{18}$FNO$_4$ | 357 |
|---|---|---|
| Found: | GC—MS | 357 |
| nuclear magnetic resonance (CDCl$_3$): | δ 0.95 (d, 6, HC(CH$_3$)$_2$) | |
| | δ 1.75 (d, 2, OC$\underline{H}$CH$_3$) | |
| | δ 3.95 (d, 1, $\underline{H}$C(CH$_3$)$_2$) | |
| | δ 4.75 (a, 7, OC$\underline{H}$CH$_3$) | |
| | δ 6.75–7.65 (m, 7, aromatic) | |

EXAMPLE 14

Preparation of 2-(1-methoxypropyl) 2-(4-(2'-fluoro-4'-cyanophenoxy)phenoxy)propionate The procedure of Example 10 was repeated substituting an equivalent amount of 1-methoxy-2-propanol for the n-butanol. The product was isolated as a viscous oil whose purity exceeded 99 percent by gas-chromatographic analysis.

mass spectrum: m/e 373

| infrared (Nujol): | 1750 cm$^{-1}$ | ($>$C=O) |
|---|---|---|
| | 2250 cm$^{-1}$ | (CN) |
| nuclear magnetic resonance (CDCl$_3$): | δ 1.20 (m, 3, CHC$\underline{H}_3$) | |
| | δ 1.55 (d, 3, CH$_3$) | |
| | δ 3.30 (s, 3, OCH$_3$) | |
| | δ 3.20–3.45 (m, 2, OCH$_2$) | |
| | δ 4.70 (q, 1, CH) | |
| | δ 5.20 (q, 1, OCH) | |
| | δ 6.70–7.60 (m, 7, aromatic) | |

EXAMPLE 15

Preparation of n-nonyl 2-(4-(2'-fluoro-4'-cyanophenoxy)phenoxy)propionate

The procedure of Example 10 was repeated substituting an equivalent amount of n-nonyl alcohol for the n-butanol. The product was isolated as a viscous oil whose purity exceeded 99 percent by gas-chromatographic analysis.

| mass spectrum | m/e 427 |
|---|---|
| infrared (Nujol) | 1750 cm$^{-1}$ |
| | 2250 cm$^{-1}$ |
| nuclear magnetic resonance (CDCl$_3$) | δ0.90 (t, 3 CH$_3$) |
| | δ1.22 (s, 14, CH$_2$) |
| | δ1.55 (d, 3, CH$_3$) |
| | δ4.20 (t, 2, OCH$_2$) |
| | δ4.75 (q, 1, CH) |
| | δ6.70–7.65 (m, 7, aromatic) |

EXAMPLE 16

Preparation of 2-(4-(2'-fluoro-4'-cyanophenoxy)phenoxy)propionamide 2-(4-(2'-Fluoro-4'-cyanophenoxy)phenoxy)propionic acid chloride (approx. 4 g) was dissolved in 100 mL of toluene and the solution was sparged with anhydrous ammonia in excess. The product was isolated by filtration and washing with water. After drying and recrystallization from acetone, the product had a m.p. 163°–165° C.

| mass spectrum: m/e 300 | | |
|---|---|---|
| infrared (Nujol): | 3400 cm$^{-1}$ | (NH$_2$) |
| | 3200 cm$^{-1}$ | (NH$_2$) |
| | 2250 cm$^{-1}$ | (CN) |
| | 1650 cm$^{-1}$ | ($>$C=O) |
| nuclear magnetic resonance (DMSO-d$_6$): | δ 1.45 (D, 3, CH$_3$) | |
| | δ 4.65 (q, 1, CH) | |
| | δ 6.80–8.15 (m, 9, aromatic & NH$_2$) | |

EXAMPLE 17

Preparation of N-methyl 2-(4-(2'-fluoro-4'-cyanophenoxy)phenoxy)propionamide

The procedure of Example 16 was repeated substituting anhydrous methylamine for the ammonia. The product, isolated by extraction and purified by recrystallization from acetone-hexane, had a m.p. 118°–120° C.

| mass spectrum: m/e 314 | | |
|---|---|---|
| infrared (Nujol): | 3300 cm$^{-1}$ | (NH) |
| | 2250 cm$^{-1}$ | (CN) |

| | |
|---|---|
| -continued | |
| 1650 cm$^{-1}$ | 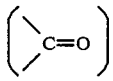 |
| nuclear magnetic resonance (DMSO-d$_6$): | δ 1.40 (d, 3, CH$_3$) |
| | δ 2.55 (d, 3, NCH$_3$) |
| | δ 4.65 (q, 1, CH) |
| | δ 6.80–8.20 (m, 7, aromatic) |

EXAMPLE 18

Preparation of N,N-dimethyl 2-(4-(2'-fluoro-4'-cyanophenoxy)phenoxy)propionamide The procedure of Example 16 was repeated substituting anhydrous dimethylamine for the ammonia. The product, isolated by extraction and purified by recrystallization from acetone-hexane, had a m.p. 93°–95° C.

| | | |
|---|---|---|
| mass spectrum: m/e 328 | | |
| infrared (Nujol): | 2240 cm$^{-1}$ | (CN) |
| | 1655 cm$^{-1}$ | 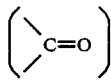 |
| nuclear magnetic resonance: | δ 1.45 (d, 3, CH$_3$) | |
| | δ 3.00 (d, 6, N(CH$_3$)$_2$) | |
| | δ 5.25 (q, 1, CH) | |
| | δ 6.70–8.15 (m, 7, aromatic) | |

The compounds of the present invention, i.e., active ingredients, have been found to be suitable for use in methods for the postemergent control of grasses, such as, barnyard grass, crabgrass, and Johnson grass, in the presence of broadleaf crops, such as, cotton, soybeans and sugar beets. Further, it has been surprisingly found that the compounds of Formula (I) above are selective, i.e., exhibit little or no phytotoxic effects, to wheat, barley and especially rice at concentrations that control undesired weed grasses.

For all such uses, unmodified active ingredients of the present invention can be employed. However, the present invention embraces the use of a herbicidally-effective amount of the active ingredients in composition form with an inert material known in the art as an agricultural adjuvant or carrier in solid or liquid form. Such adjuvants or carriers must not be phytotoxic to valuable crops particularly at the concentration employed in applying the composition in attempting selective weed control in the presence of crops. If weed control is desired in the absence of crops, it is generally sufficient to employ adjuvants or carriers which do not leave a persistent phytotoxic residue.

Thus, for example, an active ingredient can be dispersed on a finely-divided solid and employed therein as a dust. Also, the active ingredients, as liquid concentrates or solid compositions comprising one or more of the active ingredients can be dispersed in water, typically with aid of a wetting agent, and the resulting aqueous dispersion employed as a spray. In other procedures the active ingredients can be employed as a constituent of organic liquid compositions, oil-in-water and water-in-oil emulsions or dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

Organic solvents that can be employed include toluene, xylene, kerosene, diesel fuel, fuel oil, and petroleum naphtha, ketones such as acetone, methylethyl ketone and cyclohexanone, chlorinated hydrocarbons such as trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butylcarbitol acetate and glycerine. Mixtures of water and organic solvents, either as emulsions or solutions, can be employed.

The active ingredients of the present invention can also be applied as aerosols, e.g., by dispersing them by means of a compressed gas such as one of the fluorocarbons or one of its hydrocarbon successors.

The active ingredients of the present invention can also be applied with solid adjuvants or carriers such as talc, pyrophyllite, synthetic fine silica, attapulgus clay, kieselguhr, chalk, diatomaceous earth, lime, calcium cabonate, bentonite Fuller's earth, cotton seed hulls, wheat flour, soybean flour, pumice, tripoli, wood flour, walnut shell flour, redwood flour and lignin.

As stated, it is frequently desirable to incorporate a surface-active agent in the compositions of the present invention. Such surface-active or wetting agents are advantageously employed in both the solid and liquid compositions. The surface-active agent can be anionic, cationic or nonionic in character.

Typical classes of surface-active agents include alkyl sulfonate salts, alkylaryl sulfonate salts, alkylaryl polyether alcohols, fatty acid esters of polyhydric alcohols and the alkylene oxide addition products of such esters, and addition products of long-chain mercaptans and alkylene oxides. Typical examples of such surface-active agents include the sodium alkylbenzene sulfonates having 10 to 18 carbon atoms in the alkyl group, alkyl phenol ethylene oxide condensation products, e.g., p-isooctylphenol condensed with 20 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decyl sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, sodium dibutylnaphthalene sulfonate, sodium lignin sulfonate, polyethylene glycol stearate, sodium dodecyl benzene sulfonate, tertiary dodecyl polyethylene glycol thioether (nonionic 218), long-chain ethylene oxidepropylene oxide and condensation products, e.g., Pluronic 61 (molecular weight about 1000), polyethylene glycol ester of tall oil acids, sodium octophenoxyethoxyethyl sulfate, tris(polyoxyethylene)sorbitan monostearate (Tween 60), and sodium dihexylsulfosuccinate.

The concentration of the active ingredients in solid or liquid compositions generally is from about 0.003 to about 95 percent by weight or more. Concentrations from about 0.05 to about 50 percent by weight are often employed. In compositions to be employed as concentrates, the active ingredient can be present in a concentration from about 5 to about 98 weight percent, preferably 15–50 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of powder dusters, boom and hand sprayers, spray dusters, granule applicators, by addition to irrigation water, by hand application as in the case of granules, and by other conventional means. The compositions can also be applied from airplanes as a dust or spray since the active ingredients are effective at very low application rates.

In the following illustrative compositions, parts and percentages are by weight.

EMULSIFIABLE CONCENTRATES

Formulation A

| | WT % |
|---|---|
| R-enantiomer of methyl 2-(4-(2'-fluoro-4'-cyanophenoxy)phenoxy)propionate | 26.2 |
| Polyglycol 26-3 Nonionic emulsifier-(di-sec-butyl)-phenyl-poly(oxypropylene)block polymer with (oxyethylene). The polyoxyethylene content is about 12 moles. | 5.2 |
| Witconate P12-20 (Anionic emulsifier-calcium dodecylbenzene sulfonate - 60 wt. % active) | 5.2 |
| Aromatic 100 (Xylene range aromatic solvent) | 63.4 |

Formulation B

| | WT % |
|---|---|
| R-enantiomer of methyl 2-(4-(2'-fluoro-4'-cyanophenoxy)phenoxy)propionate | 3.46 |
| Sunspray 11N (paraffin oil) | 40.00 |
| Polyglycol 26-2 | 19.00 |
| Oleic acid | 1.00 |
| Xylene range aromatic solvent | 36.54 |

Formulation C

| | WT % |
|---|---|
| Methyl 2-(4-(2'-fluoro-4'-cyanophenoxy)phenoxy)propionate | 13.2 |
| Stepon C-65 | 25.7 |
| Ethomeen T/25 | 7.7 |
| Ethomeen T/15 | 18.0 |
| Xylene range aromatic solvent | 35.4 |

These concentrates can be diluted with water to give emulsions of suitable concentrations for controlling grassy weeds in cultivations of plants.

WETTABLE POWDERS

Formulation D

| | WT % |
|---|---|
| Methyl 2-(4-(2'-fluoro-4'-cyanophenoxy)phenoxy)propionate | 25.99 |
| Polyglycol 26-3 | 2.00 |
| Polyfon H | 4.00 |
| Zeosyl 100 (Precipitated hydrated $SiO_2$) | 17.00 |
| Barden clay + inerts | 51.01 |

Formulation E

| | WT % |
|---|---|
| Methyl 2-(4-(2'-fluoro-4'-cyanophenoxy)phenoxy)propionate | 62.37 |
| Polyfon H (sodium salt of lignin sulfonate) | 6.00 |
| Sellogen HR (sodium naphthalene sulfonate) | 4.00 |
| Zeosyl 100 | 27.63 |

The active ingredient is applied to the corresponding carriers and then these are mixed and ground to yield wettable powders of excellent wettability and suspension power. By diluting these wettable powders with water, it is possible to obtain suspensions of suitable concentrations for controlling grassy weeds in cultivations of plants.

WATER DISPERSIBLE GRANULES

Formulation F

| | WT % |
|---|---|
| Methyl 2-(4-(2'-fluoro-4'-cyanophenoxy)phenoxy)propionate | 26.0 |
| Sellogen HR | 4.0 |
| Polyfon H | 5.0 |
| Zeosyl 100 | 17.0 |
| Kaolinite clay | 48.0 |

The active ingredient is applied in a liquid state to the hydrated silica which is then mixed with the other ingredients and ground to a powder. The powder is agglomerated with water and sieved to provide granules in the range of −10 to +60 mesh. By dispersing these granules in water it is possible to obtain suspensions of suitable concentrations for controlling grassy weeds in cultivations of plants.

GRANULES

Formulation G

| | WT % |
|---|---|
| Methyl 2-(4-(2'-fluoro-4'-cyano phenoxy)phenoxy)propionate | 5.0 |
| Celetom MP-88 | 95.0 |

The active ingredient is applied in a liquid state to the Celetom MP-88 carrier or to other suitable carriers. The resulting granules can be applied directly to paddy rice water by hand, granule applicator, airplane, etc. in order to control grassy weeds in rice.

Formulation H

|  | WT % |
|---|---|
| Methyl 2-(4-(2'-fluoro-4'-cyanophenoxy)phenoxy)propionate | 1.0 |
| Polyfon H | 8.0 |
| Nekal BA 77 | 2.0 |
| Zinc Sterate | 2.0 |
| Barden Clay | 87.0 |

All materials are blended, ground to a powder, then water is added and the clay mixture is stirred until a paste is formed. The mixture is extruded through a die to provide granules of proper size for direct application to paddy water.

The active ingredients of the present invention have been found to possess desirable herbicidal activity in general against grassy weeds such as foxtail, wild oats, barnyard grass and crabgrass in postemergent operations. The active ingredients possess desirable herbicidal activity against the grassy weeds, described above, while at the same time are tolerant or selective to broadleaf crops, such as, cotton and soybeans. The compounds of Formula (I) are surprisingly tolerant or selective to wheat, barley and especially rice.

The exact rate to be applied is dependent not only on a specific active ingredient being applied, but also on a particular action desired (e.g., general or selective control), the plant species to be modified, and the stage of growth thereof as well as the part of the plant to be contacted with the toxic active ingredient. Thus, it is to be understood that all of the active ingredients of the present invention and compositions containing the same may not be equally effective at similar concentrations or against the same plant species.

In non-selective postemergent operations a dosage of about 0.001 to about 20 kilograms/hectare or more is generally applicable, although not all compounds are equally effective and some weeds are more difficult to control. A dosage rate in the range of about 0.01 to about 1.0 kilograms/hectare is preferred in selective postemergent control of annual grassy weeds, while about 0.025 to about 5 kilograms/hectare is preferred and more preferably about 0.05 to about 2 kilograms/hectare for the selective postemergent control of perennial grassy weeds.

In general, foliar treatments are preferred to soil treatments.

EXAMPLE A

Postemergent Activity

Representative compositions of the present invention were evaluated for the postemergence control of species of plants listed in Table A. In these evaluations, plots of the plant species listed in Table A, grown to a height of about 4 inches, were used. Aqueous spray compositions, containing various amounts of 2-(4-(2'-fluoro-4'-cyanophenoxy)phenoxy)propionic acid methyl ester, i.e., 1000 ppm, 500 ppm, 250 ppm, 125 ppm, 62.5 ppm and 31.25 ppm, respectively, were applied to separate plots. The spray compositions were made by mixing the active ingredient in acetone to ½ the final volume, i.e., twice the final concentration. An equal amount of aqueous spray solution was added to the active ingredient/acetone mixture wherein the aqueous spray solution contained 20 percent iso-propyl alcohol, 2 percent crop oil concentrate and 0.04 percent Triton ® X-155. The application to the plants was made to the point of runoff and was carried out with a hand-held syringe. Other plots were sprayed with similar compositions containing no toxicant to serve as controls. Thereafter, the plots were maintained under conditions conducive for plant growth. Two weeks after treatment, the plots were examined for plant growth and evaluated on a scale of 0 to 100 where 0 represents no effect and 100 represents complete kill. The results of the examination of the treated plots are set forth below in Table A.

®Trademark of Rohm and Haas Company

TABLE A

Percent Kill and Control of Plants at Various Concentrations (ppm) of Methyl 2-(4-(2'-fluoro-4'-cyanophenoxy)phenoxy)propionate

| Plant | Control | 1000 | 500 | 250 | 125 | 62.5 | 31.25 |
|---|---|---|---|---|---|---|---|
| Rape | 0 | 60 | 60 | 0 | 0 | 0 | 0 |
| Velvet leaf | 0 | 30 | 20 | 20 | 0 | 0 | 0 |
| Corn | 0 | 80 | 80 | 80 | 70 | 70 | 70 |
| Rice | 0 | 0 | 0 | 0 | 0 | 0 | 0 |
| Sorghum | 0 | 80 | 80 | 70 | 70 | 70 | 40 |
| Wheat* | 0 | 0 | 0 | 0 | 0 | 0 | 0 |
| Barnyard Grass | 0 | 100 | 100 | 90 | 70 | 70 | 0 |
| Crabgrass | 0 | 80 | 70 | 30 | 0 | 0 | 0 |
| Giant Foxtail | 0 | 100 | 80 | 70 | 60 | 60 | 20 |
| Johnson Grass | 0 | 100 | 100 | 90 | 40 | 60 | 0 |
| Wild Oats | 0 | 40 | 40 | 60 | 40 | 40 | 0 |
| Yellow Foxtail | 0 | 100 | 90 | 75 | 70 | 70 | 20 |

*in other tests slight phytotoxicity to wheat has been observed at the high dose rates At 1000 ppm and below, methyl 2-(4-(2'-fluoro-4'-cyanophenoxy)phenoxy)propionate was also selective, i.e., no phytotoxic effect, to cotton, soybeans, sugar beets, jimsonweed, morning glory, pigweed, cocklebur, lambsquarters, wild buckwheat, coffeeweed and yellow nutsedge.

By applying the well-accepted probit analysis as described by J. Berkson in Journal of the American Statistical Association, 48, 565 (1953) and by D. Finney in "Probit Analysis" Cambridge University Press (1952), the above data can be used to calculate $GR_{50}$ and $GR_{80}$ values, which are defined as growth reduction factors that correspond to the effective dose of herbicide required to kill or control 50 percent or 80 percent, respectively, of a target plant. From the above data, a $GR_{50}$ of about 132 ppm and a $GR_{80}$ of about 546 ppm with respect to grassy weeds can be calculated.

EXAMPLE B

Postemergent Activity

Substantially the same procedures as those described in Example A were repeated except that the active ingredient was the optically active R-enantiomer of 2-(4-(2'-fluoro-4'-cycanophenoxy)phenoxy)propionic acid methyl ester. The results are listed in Table B.

TABLE B

Percent Kill and Control of Plants at Various Concentrations (ppm) of R-Methyl 2-(4-(2'-fluoro-4'-cyanophenoxy)phenoxy)propionate

| Plant | Control | 1000 | 500 | 250 | 125 | 62.5 | 31.25 |
|---|---|---|---|---|---|---|---|
| Rape | 0 | 100 | 70 | 30 | 0 | 0 | 0 |
| Velvetleaf | 0 | 20 | 30 | 15 | 0 | 0 | 0 |
| Corn | 0 | 100 | 80 | 80 | 70 | 70 | 65 |
| Rice | 0 | 0 | 0 | 0 | 0 | 0 | 0 |
| Sorghum | 0 | 80 | 80 | 70 | 70 | 70 | 50 |
| Wheat | 0 | 45 | 20 | 0 | 0 | 0 | 0 |
| Barnyard Grass | 0 | 100 | 100 | 90 | 85 | 80 | 65 |
| Crabgrass | 0 | 80 | 70 | 60 | 60 | 25 | 0 |
| Giant Foxtail | 0 | 100 | 100 | 80 | 60 | 60 | 30 |
| Johnson Grass | 0 | 100 | 100 | 85 | 70 | 70 | 60 |
| Wild Oats | 0 | 80 | 70 | 70 | 40 | 40 | 20 |
| Yellow Foxtail | 0 | 100 | 100 | 85 | 80 | 70 | 60 |

At 1000 ppm and below, R-methyl 2-(4-(2'-fluoro-4'-cyanophenoxy)phenoxy)propionate was also selective to cotton, soybeans, sugar beets, jimsonweed, morning glory, coffeeweed, wild buckwheat, pigweed, cocklebur, lambsquarters and yellow nutsedge.

Against grassy weeds, $GR_{50}$ and $GR_{80}$ values of approximately 49 ppm and 327 ppm respectively can be calculated from the above data.

EXAMPLE C

Postemergent Activity Dryland Rice

The rice plants and weeds were grown in a clay loam soil. The plants were treated at the indicated leaf (lf) stage. Treatments were applied on a grams/hectare basis through a tracksprayer at an application volume of 187 liters/hectare. The R-enantiomer of methyl 2-(4-(2'-fluoro-4'-cyanophenoxy)phenoxy)propionate (90.5 percent R-configuration), as a 26.2 percent emulsifiable concentrate, was mixed with predetermined amounts of aqueous solution containing 0.25 percent non-ionic surfactant X-77* and applied at seven rates of active ingredient as a serial dilution. Evaluations were made two weeks after treatment with 0 representing no visible effect and 100 representing complete kill. The results are listed in Table C.

*Chevron Chemical Company

TABLE C

Percent Kill and Control of Grassy Weeds at Various Concentrations (g/ha) of R-Methyl 2-(4-(2'-fluoro-4'-cyanophenoxy)phenoxy)propionate

| Plant | Growth Stage at Treatment | Control | 400 | 200 | 100 | 50 | 25 | 12.5 | 6.3 |
|---|---|---|---|---|---|---|---|---|---|
| Rice | 2 lf | 0 | 0 | 0 | 0 | 0 | 0 | 0 | 0 |
| Sprangletop | 3 lf | 0 | 100 | 85 | 70 | 20 | 20 | 5 | 5 |
| Barnyard Grass | 2–3 lf | 0 | 90 | 80 | 70 | 20 | 0 | 0 | 0 |
| Jungle Rice | 2–3 lf | 0 | 99 | 88 | 95 | 70 | 45 | 43 | 0 |
| Smooth Crabgrass | 2–3 lf | 0 | 93 | 80 | 75 | 60 | 10 | 10 | 0 |
| Johnson Grass | 2–3 lf | 0 | 78 | 55 | 15 | 0 | 0 | 0 | 0 |
| Fall Panicum | 1–2 lf | 0 | 98 | 90 | 95 | 93 | 95 | 75 | 23 |
| Texas Panicum | 1–2 lf | 0 | 95 | 85 | 75 | 63 | 75 | 0 | 0 |
| Yellow Foxtail | 1–2 lf | 0 | 93 | 80 | 88 | 53 | 20 | 13 | 0 |
| Green Foxtail | 2–3 lf | 0 | 100 | 78 | 63 | 10 | 0 | 0 | 0 |
| Bermuda Grass | 1–2 lf | 0 | 88 | 73 | 80 | 73 | 45 | 50 | 0 |
| Goose Grass | 2–3 lf | 0 | 100 | 99 | 95 | 90 | 78 | 75 | 35 |
| Broadleaf Signalgrass | 2–3 lf | 0 | 95 | 78 | 88 | 83 | 55 | 50 | 25 |
| Dallis Grass | 2 lf | 0 | 28 | 25 | 10 | 0 | 0 | 0 | 0 |

EXAMPLE D

Postemergent Activity Paddy Rice-Water Injection Application

Rice plants, barnyard grass and sprangletop were grown in soil in 5 cm diameter pots until plants reached the proper growth stage for treatment (1 to 3 weeks depending on species). The plants were then transplanted in 10 cm diameter cottage cheese containers and sandy soil was added to the containers. The containers were flooded to approximately 2.5 cm depth of water and the plants were allowed to acclimate for 24 hr prior to treatment. At the time of treatment, water level was adjustd as needed so weeds were partially immersed in water but rice was still exposed. Methyl 2-(4-(2'-fluoro-4'-cyanophenoxy)phenoxy)propionate was dissolved in a predetermined amount of acetone and applied with a needle syringe into the paddy water as a grams/hectare rate. Five rates were applied at a serial dilution. Evaluations were made 2 weeks after treatment with 0 representing no visible effect and 100 representing complete kill. The results are listed in Table D.

TABLE D

Percent Kill and Control of *Echinochloa crus-galli* (Barnyard Grass) and of *Leptochloa filiformis* (Sprangletop) at Various Concentrations (grams/hectare) of Methyl 2-(4-(2'-fluoro-4'-cyanophenoxy)phenoxy)propionate in Paddy Rice

| Plant | Control | 560 | 280 | 140 | 70 | 35 |
|---|---|---|---|---|---|---|
| Rice | 0 | 0 | 0 | 0 | 0 | 0 |
| Barnyard Grass | 0 | 100 | 90 | 80 | 80 | 0 |
| Sprangletop | 0 | 100 | 70 | 50 | 25 | 25 |

$GR_{50}$ 76 g/ha, $GR_{80}$ 148 g/ha } Barnyard Grass    $GR_{80}$ 305 g/ha } Sprangletop

EXAMPLE E

Postemergent Activity Paddy Rice

Rice plants, barnyard grass and sprangletop were grown in soil in 5 cm diameter pots until plants reached the proper growth stage for treatment (1 to 3 weeks depending on species). The plants were then transplanted into 10 cm cottage cheese containers and sandy soil was added to the containers. The containers were flooded to approximately 2.5 cm depth of water and the plants were allowed to acclimate for 24 hr prior to treatment. At the time of treatment, the water level was lowered as needed so the plant leaves were exposed. A 26.2 percent emulsifiable concentrate of the R-enantiomer of methyl 2-(4-(2'-fluoro-4'-cyanophenoxy)-phenoxy)propionate (90.5 percent R-configuration) was mixed with water and 1 percent crop oil concentrate and applied with a hand syringe (spray nozzle) at predetermined concentrations of active ingredient. Five concentrations were sprayed as a serial dilution. Evaluations were made 2 weeks after treatment with 0 representing no visible effect and 100 representing complete kill. The results are listed in Table E.

TABLE E

Percent Kill and Control of *Echinochloa crus-galli* (Barnyard Grass) and of *Leptochloa filiformis* (Sprangletop) at Various Concentrations (ppm) of R-Methyl 2-(4-(2'-fluoro-4'-cyanophenoxy)phenoxy)propionate in Paddy Rice

| Plant | Control | 250 | 125 | 62 | 31 | 16 |
|---|---|---|---|---|---|---|
| Rice | 0 | 0 | 0 | 0 | 0 | 0 |
| Barnyard Grass | 0 | 87 | 85 | 55 | 35 | 17 |
| Sprangletop | 0 | 100 | 100 | 100 | 97 | 90 |

EXAMPLE F

Postemergent Activity

Substantially the same procedures as those described in Example A were repeated except that the active ingredient was the optically active R-enantiomer of 2-(4-(2'-fluoro-4'-cyanophenoxy)phenoxy)propionic acid. The results are listed in Table F.

TABLE F

Percent Kill and Control of Plants at Various Concentrations (ppm) of R-2-(4-(2'-fluoro-4'-cyanophenoxy)phenoxy)propionic acid

| Plant | Control | 250 | 125 | 62.5 | 31.25 | 15.62 | 7.8 |
|---|---|---|---|---|---|---|---|
| Corn | 0 | 90 | 90 | 80 | 70 | 40 | 0 |
| Rice | 0 | 0 | 0 | 0 | 0 | 0 | 0 |
| Sorghum | 0 | 100 | 80 | 80 | 70 | 0 | 0 |
| Wheat | 0 | 15 | 0 | 0 | 0 | 0 | 0 |
| Barnyard Grass | 0 | 90 | 80 | 80 | 65 | 0 | 0 |
| Crabgrass | 0 | 90 | 90 | 80 | 25 | 0 | 0 |
| Giant Foxtail | 0 | 90 | 90 | 80 | 75 | 60 | 0 |
| Johnson Grass | 0 | 100 | 80 | 70 | 70 | 20 | 60 |
| Wild Oats | 0 | 80 | 70 | 30 | 0 | 0 | 0 |
| Yellow Foxtail | 0 | 100 | 90 | 90 | 80 | 0 | 0 |

At 250 ppm and below, R-2-(4-(2'-fluoro-4'-cyanophenoxy)phenoxy)propionic acid was selective, i.e., no phytotoxic effect to cotton, soybeans, rape, sugar beets, coffeeweed, cocklebur, jimsonweed, lambsquarter, morning glory, pigweed, velvetleaf, wild buckwheat and yellow nutsedge.

EXAMPLE G

Postemergent Activity Paddy Rice-Water Injection Applications

Substantially the same procedures as those described in Example D were repeated except that the active ingredient was 2-(4-(2'-fluoro-4'-cyanophenoxy)-phenoxy)propionic acid. The results were listed in Table G.

TABLE G

Percent Kill and Control of *Echinochloa crus-galli* (Barnyard Grass) and of *Leptochloa filiformis* (Sprangletop) at Various Concentrations (grams/hectare) of 2-(4-(2'-fluoro-4'-cyanophenoxy)phenoxy)propionic in Paddy Rice

| Plant | Control | 560 | 280 | 140 | 70 | 35 |
|---|---|---|---|---|---|---|
| Rice | 0 | 10 | 0 | 0 | 0 | 0 |
| Barnyard Grass | 0 | 90 | 65 | 0 | 0 | 0 |
| Sprangletop | 0 | 100 | 80 | 60 | 10 | 0 |

EXAMPLE H

Postemergent Activity Wheat and Barley Crops

Substantially the same procedures as those described in Example C were utilized except that the active ingredient, methyl 2-(4-(2'-fluoro-4'-cyanophenoxy)phenoxy)propionate, was formulated as an aqueous spray composition. This spray composition was prepared as in Example A. The results are listed in Table H.

TABLE H

Percent Kill and Control of Grassy Weeds at Various Concentrations (grams/hectare) of Methyl 2-(4-(2'-fluoro-4'-cyanophenoxy)phenoxy)propionate

| Plant | Control | 1000 | 250 | 63 | 15 | 4 | 1 |
|---|---|---|---|---|---|---|---|
| Wheat | 0 | 0 | 0 | 0 | 0 | 0 | 0 |
| Barley | 0 | 3 | 0 | 0 | 0 | 0 | 0 |
| Rice | 0 | 0 | 0 | 0 | 0 | 0 | 0 |
| Barnyard Grass | 0 | 99 | 99 | 98 | 88 | 43 | 27 |
| Crabgrass | 0 | 93 | 90 | 90 | 80 | 67 | 22 |
| Yellow Foxtail | 0 | 83 | 87 | 78 | 47 | 48 | 37 |

EXAMPLE I

Postemergent Activity Paddy Rice-Water Injection Application

Substantially the same procedures as those described in Example D were repeated. The tests were conducted on rice plants and sprangletop. The sodium, ammonium and triethylammonium salts of the R-enantiomers of 2-(4-(2'-fluoro-4'-cyanophenoxy)phenoxy)propionic acid, the n-butyl, 2-(1-methoxypropyl) and n-nonyl esters of racemic 2-(4-(2'-fluoro-4'-cyanophenoxy)phenoxy)propionic acid, and the unsubstituted, N- methyl and N,N-dimethyl amides of racemic 2-(4-(2'-fluoro-4'-cyanophenoxy)phenoxy)propionamide were included in the evaluation. The results are summarized in Table I.

The N-methyl and N,N-dimethyl amides were not active below 200 g/ha in this test.

EXAMPLE J

Postemergent Activity

Substantially the same procedures as those described in Example A were repeated. A somewhat different spectrum of grassy plants were employed. The treatments were applied on a parts per million (ppm) basis. One part per million approximately corresponds to 2.6 g/ha.

The sodium, ammonium and triethylammonium salts of the R-enantiomers of 2-(4-(2'-fluoro-4'-cyanophenoxy)phenoxy)propionic acid, the n-butyl, 2-(1-methoxypropyl) and n-nonyl esters of racemic 2-(4-(2'-fluoro-4'-cyanophenoxy)phenoxy)propionic acid, and the unsubstituted, N-methyl and N,N-dimethyl amides of racemic 2-(4-(2'-fluoro-4'-cyanophenoxy)phenoxy)propionamide were included in the evaluation. The results are summarized in Table J.

TABLE I

Percent Kill and Control of *Leptochloa filiformis* (Sprangletop) at Various Concentrations of

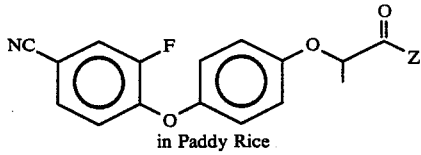

in Paddy Rice

| Z | Plant | Control | 200 | 100 | 50 | GR$_{50}$ (g/ha) |
|---|---|---|---|---|---|---|
| ONa(R) | rice | 0 | 0 | 0 | 0 | |
| | sprangletop | 0 | 98 | 70 | 17 | 76 |
| ONH$_4$(R) | rice | 0 | 10 | 0 | 0 | |
| | sprangletop | 0 | 100 | 70 | 7 | 81 |
| ONHEt$_3$(R) | rice | 0 | 0 | 0 | 0 | |
| | sprangletop | 0 | 97 | 63 | 0 | 95 |
| On-Nonyl(R,S) | rice | 0 | 10 | 0 | 0 | |
| | sprangletop | 0 | 80 | 13 | 0 | 143 |
| ![structure] (R,S) | rice | 0 | 10 | 0 | 0 | |
| | sprangletop | 0 | 100 | 58 | 0 | 97 |
| On-Bu(R,S) | rice | 0 | 0 | 0 | 0 | |
| | sprangletop | 0 | 92 | 57 | 0 | 101 |
| NH$_2$(R,S) | rice | 0 | 10 | 0 | 0 | |
| | sprangletop | 0 | 97 | 58 | 0 | 97 |

TABLE J

Percent Kill and Control of Grassy Weeds at Various Concentrations (ppm) of

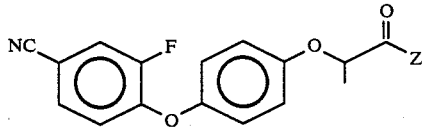

| Z | Plant | Control | 1000 | 500 | 250 | 125 | 62.5 | 31.25 | 15.62 | 7.81 |
|---|---|---|---|---|---|---|---|---|---|---|
| ONa(R) | rice | 0 | — | — | — | — | — | — | — | — |
| | wheat | 0 | — | — | — | — | — | — | — | — |
| | corn | 0 | — | — | 95 | 95 | 85 | 40 | 20 | 0 |
| | sorghum | 0 | — | — | 75 | 75 | 65 | 60 | 40 | 25 |
| | barnyard grass | 0 | — | — | 75 | 85 | 65 | 50 | 25 | 0 |
| | crabgrass | 0 | — | — | 75 | 75 | 70 | 60 | 30 | 0 |
| | giant foxtail | 0 | — | — | 75 | 75 | 70 | 60 | 50 | 0 |
| | johnson grass | 0 | — | — | 70 | 70 | 60 | 50 | 0 | 0 |
| | wild oat | 0 | — | — | 80 | 80 | 60 | 30 | 0 | 0 |
| | yellow foxtail | 0 | — | — | 60 | 60 | 50 | 40 | 0 | 0 |
| | GR$_{50}$ 54 ppm | | | | | | | | | |
| ONH$_4$ (R) | rice | 0 | — | — | 0 | 0 | 0 | 0 | 0 | 0 |
| | wheat | 0 | — | — | 0 | 0 | 0 | 0 | 0 | 0 |
| | corn | 0 | — | — | 100 | 90 | 60 | 20 | 0 | 0 |
| | sorghum | 0 | — | — | 75 | 75 | 50 | 40 | 20 | 20 |
| | barnyard grass | 0 | — | — | 80 | 80 | 50 | 40 | 40 | 0 |
| | crabgrass | 0 | — | — | 70 | 75 | 70 | 70 | 20 | 0 |
| | giant foxtail | 0 | — | — | 70 | 70 | 60 | 60 | 0 | 0 |
| | johnson grass | 0 | — | — | 70 | 70 | 60 | 60 | 50 | 30 |
| | wild oat | 0 | — | — | 60 | 60 | 40 | 0 | 0 | 0 |
| | yellow foxtail | 0 | — | — | 80 | 75 | 65 | 25 | 0 | 0 |
| | GR$_{50}$ 55 ppm | | | | | | | | | |
| ONHEt$_3$ (R) | rice | 0 | — | — | 0 | 0 | 0 | 0 | 0 | 0 |
| | wheat | 0 | — | — | 20 | 0 | 0 | 0 | 0 | 0 |
| | corn | 0 | — | — | 95 | 85 | 60 | 40 | 0 | 0 |

TABLE J-continued

Percent Kill and Control of Grassy Weeds at Various Concentrations (ppm) of $$NC\text{-}C_6H_3(F)\text{-}O\text{-}C_6H_4\text{-}O\text{-}CH(CH_3)\text{-}C(=O)\text{-}Z$$

| Z | Plant | Control | 1000 | 500 | 250 | 125 | 62.5 | 31.25 | 15.62 | 7.81 |
|---|---|---|---|---|---|---|---|---|---|---|
| | sorghum | 0 | — | — | 75 | 70 | 40 | 30 | 20 | 0 |
| | barnyard grass | 0 | — | — | 80 | 70 | 70 | 60 | 20 | 20 |
| | crabgrass | 0 | — | — | 80 | 70 | 65 | 50 | 20 | 0 |
| | giant foxtail | 0 | — | — | 80 | 70 | 70 | 70 | 50 | 0 |
| | johnson grass | 0 | — | — | 80 | 80 | 70 | 70 | 40 | 20 |
| | wild oat | 0 | — | — | 80 | 75 | 75 | 40 | 0 | 0 |
| | yellow foxtail | 0 | — | — | 60 | 50 | 50 | 20 | 20 | 0 |
| | $GR_{50}$ 47 ppm | | | | | | | | | |
| OnNonyl (R,S) | rice | 0 | — | — | 0 | 0 | 0 | 0 | 0 | 0 |
| | wheat | 0 | — | — | 20 | 0 | 0 | 0 | 0 | 0 |
| | corn | 0 | — | — | 90 | 65 | 40 | 40 | 0 | 0 |
| | sorghum | 0 | — | — | 70 | 75 | 50 | 30 | 30 | 20 |
| | barnyard grass | 0 | — | — | 90 | 75 | 50 | 30 | 20 | 0 |
| | crabgrass | 0 | — | — | 50 | 40 | 40 | 0 | 0 | 0 |
| | giant foxtail | 0 | — | — | 70 | 70 | 70 | 50 | 25 | 25 |
| | johnson grass | 0 | — | — | 70 | 70 | 65 | 50 | 25 | 25 |
| | wild oat | 0 | — | — | 70 | 70 | 50 | 20 | 0 | 0 |
| | yellow foxtail | 0 | — | — | 70 | 50 | 30 | 20 | 0 | 0 |
| | $GR_{50}$ 80 ppm | | | | | | | | | |
| O-CH₂-CH(OMe)-O (R,S) (cyclic acetal) | rice | 0 | — | — | 0 | 0 | 0 | 0 | 0 | 0 |
| | wheat | 0 | — | — | 0 | 0 | 0 | 0 | 0 | 0 |
| | corn | 0 | — | — | 90 | 90 | 90 | 60 | 20 | 0 |
| | sorghum | 0 | — | — | 65 | 50 | 50 | 40 | 20 | 20 |
| | barnyard grass | 0 | — | — | 70 | 70 | 65 | 40 | 40 | 25 |
| | crabgrass | 0 | — | — | 70 | 70 | 70 | 30 | 0 | 0 |
| | giant foxtail | 0 | — | — | 75 | 70 | 70 | 60 | 0 | 0 |
| | johnson grass | 0 | — | — | 75 | 70 | 70 | 60 | 30 | 30 |
| | wild oat | 0 | — | — | 75 | 50 | 0 | 0 | 0 | 0 |
| | yellow foxtail | 0 | — | — | 70 | 60 | 30 | 0 | 0 | 0 |
| | $GR_{50}$ 67.5 ppm | | | | | | | | | |
| On—Bu (R,S) | rice | 0 | — | — | 0 | 0 | 0 | 0 | 0 | 0 |
| | wheat | 0 | — | — | 20 | 0 | 0 | 0 | 0 | 0 |
| | corn | 0 | — | — | 95 | 70 | 60 | 50 | 0 | 0 |
| | sorghum | 0 | — | — | 60 | 50 | 70 | 30 | 20 | 20 |
| | barnyard grass | 0 | — | — | 75 | 75 | 70 | 55 | 30 | 20 |
| | crabgrass | 0 | — | — | 70 | 70 | 70 | 20 | 0 | 0 |
| | giant foxtail | 0 | — | — | 75 | 70 | 60 | 50 | 20 | 0 |
| | johnson grass | 0 | — | — | 65 | 65 | 50 | 50 | 25 | 20 |
| | wild oat | 0 | — | — | 60 | 60 | 50 | 0 | 0 | 0 |
| | yellow foxtail | 0 | — | — | 60 | 50 | 50 | 25 | 0 | 0 |
| | $GR_{50}$ 72 ppm | | | | | | | | | |
| NH₂ (R,S) | rice | 0 | 0 | 0 | 0 | 0 | 0 | 0 | — | — |
| | wheat | 0 | 0 | 0 | 0 | 0 | 0 | 0 | — | — |
| | corn | 0 | 25 | 20 | 0 | 0 | 0 | 0 | — | — |
| | sorghum | 0 | 80 | 75 | 75 | 70 | 50 | 40 | — | — |
| | barnyard grass | 0 | 60 | 50 | 50 | 30 | 0 | 0 | — | — |
| | crabgrass | 0 | 70 | 70 | 60 | 55 | 0 | 0 | — | — |
| | giant foxtail | 0 | 70 | 70 | 60 | 50 | 35 | 0 | — | — |
| | johnson grass | 0 | 65 | 65 | 65 | 50 | 50 | 40 | — | — |
| | wild oat | 0 | 60 | 60 | 40 | 0 | 0 | 0 | — | — |
| | yellow foxtail | 0 | 70 | 70 | 60 | 50 | 0 | 0 | — | — |
| | $GR_{50}$ 291 ppm | | | | | | | | | |
| NHCH₃ (R,S) | rice | 0 | 0 | 0 | 0 | 0 | 0 | 0 | — | — |
| | wheat | 0 | 0 | 0 | 0 | 0 | 0 | 0 | — | — |
| | corn | 0 | 20 | 0 | 0 | 0 | 0 | 0 | — | — |
| | sorghum | 0 | 70 | 60 | 60 | 60 | 0 | 0 | — | — |
| | barnyard grass | 0 | 20 | 0 | 0 | 0 | 0 | 0 | — | — |

TABLE J-continued

Percent Kill and Control of Grassy Weeds at Various Concentrations (ppm) of

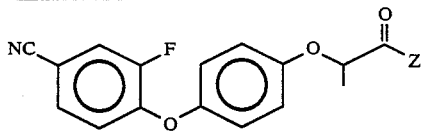

| Z | Plant | Control | 1000 | 500 | 250 | 125 | 62.5 | 31.25 | 15.62 | 7.81 |
|---|---|---|---|---|---|---|---|---|---|---|
| | crabgrass | 0 | 10 | 0 | 0 | 0 | 0 | 0 | — | — |
| | giant foxtail | 0 | 55 | 40 | 0 | 0 | 0 | 0 | — | — |
| | johnson grass | 0 | 50 | 45 | 50 | 35 | 0 | 0 | — | — |
| | wild oat | 0 | 0 | 0 | 0 | 0 | 0 | 0 | — | — |
| | yellow foxtail | 0 | 35 | 25 | 20 | 0 | 0 | 0 | — | — |
| $N(CH_3)_2$ (R,S) | rice | 0 | 0 | 0 | 0 | 0 | 0 | 0 | — | — |
| | wheat | 0 | 0 | 0 | 0 | 0 | 0 | 0 | — | — |
| | corn | 0 | 10 | 0 | 0 | 0 | 0 | 0 | — | — |
| | sorghum | 0 | 50 | 40 | 20 | 0 | 0 | 0 | — | — |
| | barnyard grass | 0 | 0 | 0 | 0 | 0 | 0 | 0 | — | — |
| | crabgrass | 0 | 30 | 10 | 0 | 0 | 0 | 0 | — | — |
| | giant foxtail | 0 | 25 | 0 | 0 | 0 | 0 | 0 | — | — |
| | johnson grass | 0 | 30 | 20 | 0 | 0 | 0 | 0 | — | — |
| | wild oat | 0 | 0 | 0 | 0 | 0 | 0 | 0 | — | — |
| | yellow foxtail | 0 | 0 | 0 | 0 | 0 | 0 | 0 | — | — |

EXAMPLE K

Postemergent Activity Dryland Rice

Substantially the same procedures as those described in Example C were repeated. The tests were conducted on rice plants, barnyard grass and sprangletop. The methyl, iso-propyl, sec-butyl and iso-butyl esters of racemic 2-(4-(2'-fluoro-4'-cyanophenoxy)phenoxy)propionic acid were included in the evaluation. The results are summarized in Table K.

TABLE K

Percent Kill and Control of *Echinochloa crus-galli* (Barnyard Grass) and of *Leptochloa filiformis* (Sprangletop) at Various Concentrations of

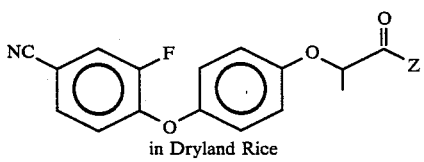

in Dryland Rice

| | | | Concentration (g/ha) | | | | | |
|---|---|---|---|---|---|---|---|---|
| Z | Plant | Control | 400 | 200 | 100 | 50 | 25 | $GR_{80}$ (g/ha) |
| O—Me | rice | 0 | 0 | 0 | 0 | 0 | 0 | >400 |
| | barnyard grass | 0 | 98 | 75 | 73 | 60 | 65 | 135 |
| | sprangletop | 0 | 100 | 98 | 95 | 78 | 40 | 63 |
| O—iso-Pr | rice | 0 | 0 | 0 | 0 | 0 | 0 | >400 |
| | barnyard grass | 0 | 95 | 70 | 73 | 60 | 55 | 155 |
| | sprangletop | 0 | 95 | 93 | 80 | 60 | 30 | 100 |
| O—iso-Bu | rice | 0 | 0 | 0 | 0 | 0 | 0 | >400 |
| | barnyard grass | 0 | 88 | 88 | 75 | 63 | 45 | 148 |
| | sprangletop | 0 | 93 | 75 | 60 | 40 | 20 | 206 |
| O—sec-Bu | rice | 0 | 0 | 0 | 0 | 0 | 0 | >400 |
| | barnyard grass | 0 | 90 | 75 | 73 | 70 | 68 | 165 |
| | sprangletop | 0 | 99 | 85 | 60 | 60 | 20 | 157 |

The compounds of the present invention contain an optically active center as shown in Formula III (2-position of the propionic acid) and can exist in optically active stereoisomeric forms. The R-enantiomers are distinguished by enhanced herbicidal activity. Both the pure enantiomers and various mixtures thereof are within the scope of the present invention.

In further embodiments, the compounds of the present invention or compositions containing the same, can be advantageously employed in combination with one or more additional pesticidal compounds. Such additional pesticidal compounds may be insecticides, nematicides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use, or as an additament. The compounds in combination can generally be present in the ratio of from 1 to 100 parts of the compound of the present invention with from 100 to 1 parts of the additional compound(s).

The purpose of lowering the labor for application or of increasing the spectrum of effectively removable weed species, it is sometimes preferable to provide mixtures of the active ingredients with other complementary herbicides. Complementary herbicides that can be mixed with the active ingredients include but are not limited to the following compounds:

Methyl 2-(((((4,6-dimethoxypyrimidin-2-yl)amino)carbonyl)amino)sulfonyl)methyl)benzoate 3-Isopropyl-1H-2,1,3-benzothiadiazin-4(3H)one-2,2-dioxide (bentazon)

Ethyl 5-[3-(4,6-dimethoxypyrimidin-2-yl)ureidosulfonyl]-1-methylpyrazole-4-carboxylate (NC-311)

2-(3,5-Dichlorophenyl)-2-(2,2,2-trichloroethyl)oxirane (tridiphane)

4-Amino-3,5-dichloro-6-fluoro-2-pyridinyloxyacetic acid (fluoroxypyr)

3,5,6-Trichloro-2-pyridinyloxyacetic acid (triclopyr)

Methyl 2-[4-((3-chloro-5-(trifluoromethyl)-2-pyridinyl)oxy)phenoxy]propionate (haloxyfop)

N-(3,4-dichlorophenyl)propanamide (propanil)

The active ingredients of Formula (II) can be hydrolyzed and/or oxidized in the plants or soil to a carboxyl moiety that, depending on the pH, is in the undissociated and/or dissociated form. For example, an ester —COOR³ or an amide —CONR³R⁴ can be hydrolyzed in the soil or the plant to the acid —COOH, which, depending on the pH, is in the undissociated —COOH form, the dissociated —COO⊖ form or an equilibrium mixture of both forms. Similarly, a valeric acid —CH(CH₃)CH₂CH₂COOH, for example, can be oxidized by microbial or plant metabolic β-oxidation to the corresponding propionic acid —CH(CH₃)COOH. In the most preferred embodiment of this invention, it is the propionic acid of Formula (III) that is the actual toxaphore in the grassy weeds. This can be generally established by studies in which the carboxylic acid in its undissociated and/or dissociated form or as a derivative thereof is the most prevalent species detected within the plant. Since the agriculturally acceptable derivatives of Formula (II) are subject to such processes, the present invention contemplates a method of killing and/or controlling the growth of undesired grassy plants which comprises providing in said plants a herbicidally effective amount of a compound in the acid or salt form having the formula

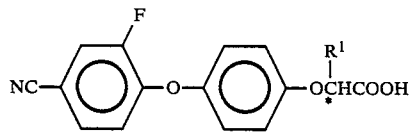

wherein R¹ is C₁-C₃ alkyl.

Various modifications may be made in the present invention without departing from the spirit or the scope thereof and it is understood that we limit ourselves only as defined in the appended claims.

What is claimed is:

1. A herbicidally active compound or a resolved optically-active isomer thereof having the formula

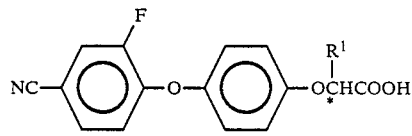

wherein R¹ represents a C₁-C₃ alkyl group; or an agriculturally acceptable derivative of the alkanoic acid group thereof that can be hydrolyzed and/or oxidized in plants or soil to said alkanoic acid moiety that, depending on the pH, is in the undissociated and/or dissociated form.

2. A compound of claim 1 which is the R-enantiomer.

3. A compound of claim 1 which is 2-(4-(2'-fluoro-4'-cyanophenoxy)phenoxy)propionic acid or an agriculturally acceptable salt or ester thereof.

4. A compound of claim 3 which is the R-enantiomer.

5. A compound of claim 2 which is the methyl, ethyl, propyl or butyl ester.

6. A compound of claim 5 which is the R-enantiomer.

7. The compound of claim 5 which is 2-(4-(2'-fluoro-4'-cyanophenoxy)phenoxy)propionic acid methyl ester.

8. The compound of claim 7 which is the R-enantiomer.

9. A composition comprising a herbicidally effective amount of one or more active compounds of claim 1 together with an agriculturally acceptable adjuvant, carrier or diluent.

10. A composition of claim 9 wherein the active compound is the R-enantiomer.

11. A composition of claim 9 wherein the active compound is 2-(4-(2'-fluoro-4'-cyanophenoxy)phenoxy)propionic acid or an agriculturally acceptable salt or ester thereof.

12. A composition of claim 11 wherein the active compound is the R-enantiomer.

13. A composition of claim 11 wherein the active compound is the methyl, ethyl, propyl or butyl ester.

14. A composition of claim 13 wherein the active compound is the R-enantiomer.

15. A composition of claim 13 wherein the active compound is 2-(4-(2'-fluoro-4'-cyanophenoxy)phenoxy)propionic acid methyl ester.

16. A composition of claim 15 wherein the active compound is the R-enantiomer.

17. A method of killing or controlling grassy weeds which comprises applying to the locus of the grassy weeds a composition as claimed in claim 9.

18. A method as claimed in claim 17 wherein the composition is applied postemergently.

19. A method as claimed in claim 18 wherein the composition is applied postemergently to control undesired grassy vegetation in the presence of broadleaf crops.

20. A method as claimed in claim 18 wherein the composition is applied postemergently to control undesired grassy vegetation in the presence of wheat, barley or rice.

21. A method as claimed in claim 20 wherein the composition is applied postemergently to control undesired grassy vegetation in the presence of rice.

22. A method as claimed in claim 21 wherein the composition contains the active compound 2-(4-(2'-fluoro-4'-cyanophenoxy)phenoxy)propionic acid or an agriculturally acceptable salt or ester thereof.

23. A method as claimed in claim 22 wherein the active compound is the R-enantiomer.

24. A method as claimed in claim 22 wherein the active compound is the methyl, ethyl, propyl or butyl ester.

25. A method as claimed in claim 24 wherein the active compound is the R-enantiomer.

26. A method as claimed in claim 24 wherein the active compound is 2-(4-(2'-fluoro-4'-cyanophenoxy)-phenoxy)propionic acid methyl ester.

27. A method as claimed in claim 26 wherein the active compound is the R-enantiomer.

28. A method of killing or controlling undesired grassy vegetation, which method comprises prividing in the vegetation a compound in the undissociated and/or dissociated form of the formula

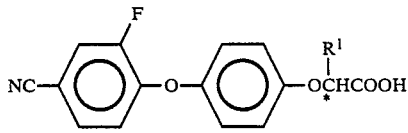

wherein $R^1$ represents a $C_1$–$C_3$ alkyl.

29. A method of killing or controlling undesired grassy vegetation, which method comprises providing in the vegetation 2-(4-(2'-fluoro-4'-cyanophenoxy)-phenoxy)propionic acid in the undissociated and/or dissociated form.

30. The compound of claim 5 which is 2-(4-(2'-fluoro-4'-cyanophenoxy)phenoxy)propionic acid n-butyl ester.

31. The compound of claim 30 which is the R-enantiomer.

32. A composition of claim 13 wherein the active compound is 2-(4-(2'-fluoro-4'-cyanophenoxy)phenoxy)propionic acid n-butyl ester.

33. A composition of claim 32 wherein the active compound is the R-enantiomer.

34. A method as claimed in claim 24 wherein the active compound is 2-(4-(2'-fluoro-4'-cyanophenoxy)-phenoxy)propionic acid n-butyl ester.

35. A method as claimed in claim 34 wherein the active compound is the R-enantiomer.

* * * * *